(12) United States Patent
Poncelet et al.

(10) Patent No.: US 8,148,459 B2
(45) Date of Patent: *Apr. 3, 2012

(54) USE OF A METAL ORGANOSILICATE POLYMER AS DISPERSION-FORMING AGENT

(75) Inventors: Olivier Poncelet, Grenoble (FR); Olivier Raccurt, Chelieu (FR); Olivier Renard, Fontanil-Cornillon (FR)

(73) Assignee: Commissariat a l'Energie Atomique (FR)

( * ) Notice: Subject to any disclaimer, the term of this patent is extended or adjusted under 35 U.S.C. 154(b) by 437 days.

This patent is subject to a terminal disclaimer.

(21) Appl. No.: 12/329,235

(22) Filed: Dec. 5, 2008

(65) Prior Publication Data

US 2009/0209684 A1    Aug. 20, 2009

(30) Foreign Application Priority Data

Dec. 19, 2007    (FR) ..................... 07 08905

(51) Int. Cl.
*C08L 83/02* (2006.01)
(52) U.S. Cl. .................................. 524/588; 106/287.1
(58) Field of Classification Search ............... 106/287.1; 524/588
See application file for complete search history.

(56) References Cited

FOREIGN PATENT DOCUMENTS

| EP | 396 237 | * 11/1990 |
| EP | 1 371 357 A | 12/2003 |
| FR | 2 848 879 A | 6/2004 |
| WO | WO 01/05362 | 1/2001 |

OTHER PUBLICATIONS

International Search Report from corresponding foreign priority French Application No. 07 08905, filed Dec. 19, 2007.
Schmidt D F et al: "On the origins of silicate dispersion in polysiloxane/layered-silicate nanocomposites"; Advanced Functional Materials, Wiley, VCH, Wienheim, DE; vol. 16, No. 3; Feb. 3, 2006; pp. 417-425; XP001238617.

* cited by examiner

*Primary Examiner* — Kuo-Liang Peng
(74) *Attorney, Agent, or Firm* — Alston & Bird LLP

(57) ABSTRACT

The invention relates to the use of a metal organosilicate polymer as a dispersion-forming agent. The metal organosilicate polymer used in the invention has one of the following formulae I and II:

$R_4Si_4Al_2O_8(OH)_x$    Formula I:

$R_8Si_8M_6O_{16}(OH)_y$    Formula II:

The invention finds application in the field of dispersions of hydrophobic compounds in water and of organophobic compounds in an organic solvent, in particular.

15 Claims, No Drawings

USE OF A METAL ORGANOSILICATE POLYMER AS DISPERSION-FORMING AGENT

CROSS REFERENCE TO RELATED APPLICATIONS

This application claims priority from French Application No. 07 08905, filed Dec. 19, 2007.

FIELD AND BACKGROUND OF THE INVENTION

The invention relates to the use of a metal organosilicate polymer as an agent for forming a dispersion of a hydrophobic material in water or a dispersion of an organophobic material in an organic solvent.

It relates more particularly to an aqueous dispersion of carbon nanotubes and an aqueous dispersion of benzotriazole, and also to the use of the aqueous dispersion of benzotriazole for the production of a composition for protection against UV radiation.

It is very difficult to disperse particles of hydrophobic compounds in an aqueous phase or to disperse particles of hydrophilic or organophobic compounds in an organic phase.

Many organic compounds are water-insoluble.

This is true of the compounds of the benzotriazole group, and more particularly of 2-(2'-hydroxy-5'-methylphenyl)benzotriazole.

Now, 2-(2'-hydroxy-5'-methylphenyl)benzotriazole consumes the photons emitted by UV rays while at the same time regenerating. It is therefore a molecule which is of great interest for the protection of various elements and supports against UV radiation since it is not consumed by UV irradiation.

However, this molecule is not water-dispersible and cannot be applied simply and in a harmless manner to the elements to be protected.

Carbon nanotubes are, for their part, inorganic materials representative of hydrophobic compounds that are difficult to disperse in water.

In general, in order to obtain a dispersion of carbon nanotubes in water, OH groups are generated at the surface of the carbon nanotubes and then these OH groups are oxidized so as to form carboxylic groups and, finally, they are converted to salts. The nanotubes are then water-"dispersible".

However, this requires many chemical reactions.

Moreover, a group of compounds referred to equally as metal organosilicate, metal phyllosilicate clay, metal organosilicate polymer or polysilsesquioxane salt, is known.

For example, U.S. Pat. No. 7,132,165 B2 describes the production of compounds of this type from amide surfactants or structuring agents. These compounds are described as being lamellar silica-based mesoporous compounds with high temperature and hydrothermal stability.

These compounds are also described by L. Ukrainczyk et al., in "Template Synthesis and Characterization of Layered Al- and Mg-Silsesquioxanes", *J. Phys. Chem. B* 1997, 101, 531-539.

A method for preparing these compounds is described in this document: the silsesquioxane compounds were prepared by precipitation at ambient temperature by adding an aqueous base to a solution of alcohol containing a mixture of $AlCl_3$ or $MgCl_2$ and a trialkoxysilane with n-dodecyl, n-octyl, n-pentyl, 3-methacryloxypropyl, isobutyl or phenyl functionality.

These compounds are described as being usable as absorbent materials, environmental barriers, polymer fillers, catalytic supports or chemical sensors.

Nicola T. Whilton et al., in "Hybrid lamellar nanocomposites based on organically functionalized magnesium phyllosilicate clays with interlayer reactivity", *J. Mater. Chem.*, 1998, 8(8), 1927-1932, also described the preparation of such compounds by the addition of organotrialkoxysilane to a solution of $MgCl_2.6H_2O$ in ethanol and precipitation with a sodium hydroxide solution.

However, in this document, no application is described or suggested for these compounds.

SUMMARY OF THE INVENTION

The invention aims to provide dispersions of hydrophobic compounds in an aqueous phase or of organophobic compounds in an organic phase.

To this effect, the invention proposes to use particles of at least one metal organosilicate polymer having one of the following formulae I and II:

$R_4Si_4Al_2O_8(OH)_x$,  Formula I:

$R_8Si_8M_6O_{16}(OH)_y$,  Formula II:

in which:
each R is, independently of the others, a group chosen from the group composed of a substituted or unsubstituted, linear or branched alkyl group, a substituted or unsubstituted, linear or branched alkenyl group, a substituted or unsubstituted aryl group, a substituted or unsubstituted benzyl group, a substituted or unsubstituted vinyl group, a substituted or unsubstituted polyaromatic group and a substituted or unsubstituted allyl group, $X \geq 2$, $y \geq 2$, in formula I, the Si/Al molar ratio is between 1.8 and 1.3 inclusive, in formula II, M is chosen from the group composed of calcium, magnesium, zinc and strontium and mixtures of two or more thereof, and the Si/M molar ratio is between 1.8 and 1.3 inclusive, as an agent for forming a dispersion of a hydrophobic material in water or a dispersion of an organophobic material in an organic solvent.

Preferably, in formulae I and II, each R is, independently of the others, chosen from a substituted or unsubstituted methyl group, a substituted or unsubstituted ethyl group, a substituted or unsubstituted n-propyl group, a substituted or unsubstituted benzyl group and a substituted or unsubstituted vinyl group.

In formulae I and II, when R is substituted, it is substituted with at least one substituent chosen from the group formed by an amino group, a halogen atom, an ether group, an ester group, a hydroxyl group, an acrylate group, an epoxy group, an alkyl group, an alkyl acrylate group, an aminoalkyl group, a chloroalkyl group, a carboxylic group, a sulfonic group and a phosphonic group.

In one preferred embodiment, the invention provides an aqueous dispersion of particles of a hydrophobic material, which comprises:
particles of at least one hydrophobic material, and
particles of at least one metal organosilicate polymer having one of the following formulae I and II:

$R_4Si_4Al_2O_8(OH)_x$,  Formula I:

$R_8Si_8M_6O_{16}(OH)_y$,  Formula II:

in which:
each R is, independently of the others, a group chosen from the group composed of a substituted or unsubstituted, linear or branched alkyl group, a substituted or unsubstituted, linear or branched alkenyl group, a substituted or unsubstituted aryl group, a substituted or unsubstituted benzyl group, a substituted or unsubstituted vinyl group, a substituted or unsubstituted polyaromatic group and a substituted or unsubstituted allyl group, $x \geq 2$, $y \geq 4$, in formula I, the Si/Al molar ratio is between 1.8 and 1.3 inclusive, in formula II, M is chosen from the group composed of calcium, magnesium, zinc and strontium and mixtures of two or more thereof, and the Si/M molar ratio is between 1.8 and 1.3 inclusive.

In this first preferred embodiment, in formulae I and II, each R is, independently of the others, preferably chosen from a substituted or unsubstituted methyl group, a substituted or unsubstituted ethyl group, a substituted or unsubstituted n-propyl group, a substituted or unsubstituted benzyl group and a substituted or unsubstituted vinyl group.

Still in this first preferred embodiment, when R is substituted, it is preferably substituted with a group formed by an amino group, a halogen atom, an ether group, an ester group, a hydroxyl group, an acrylate group, an epoxy group, an alkyl group, an alkyl acrylate group, an aminoalkyl group, a chloroalkyl group, a sulfonic group, a carboxylic group and a phosphonic group.

In a first variant of the first preferred embodiment, the particles of hydrophobic material are carbon nanotubes.

In this variant, the metal organosilicate polymer is preferably of formula II in which M is magnesium and four of the R groups are $(CH_2)_3NH(CH_3)$ groups and four of the R groups are $C_6H_5$ groups.

Still in this first variant, another preferred metal organosilicate polymer is of formula II in which M is Mg and four of the R groups are 3-aminopropyl groups and four of the R groups are phenyl groups.

However, yet another preferred metal organosilicate polymer is of formula II in which M is Mg and four of the R groups are 3-aminopropyl groups and four of the R groups are vinyl groups.

Still in this variant, the mass of carbon nanotubes/mass of metal organosilicate polymer ratio is preferably greater than or equal to 0.5.

More preferably, the mass of carbon nanotubes/mass of metal organosilicate polymer ratio is equal to 0.8.

In a second variant of the first preferred embodiment of the invention, the hydrophobic material is 2-(2'-hydroxy-5'-methylphenyl)benzotriazole, and it is obtained in an aqueous dispersion.

In this case, the metal organosilicate polymer is preferably of formula II in which M is zinc and four of the R groups are $(CH_2)_3NH(CH_3)$ groups and four of the R groups are $C_6H_5$ groups.

The invention also provides the use of the aqueous dispersion according to the second variant of the invention, for the production of a composition for protecting against UV radiation.

The invention will be understood more clearly and other characteristics and advantages thereof will emerge more clearly on reading the explanatory description which follows.

The metal organosilicate polymers used in the invention have one of the following formulae I and II below:

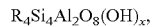  Formula I:

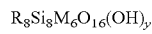  Formula II:

in which:
each R is, independently of the others, a group chosen from the group composed of a substituted or unsubstituted, linear or branched alkyl group, a substituted or unsubstituted, linear or branched alkenyl group, a substituted or unsubstituted aryl group, a substituted or unsubstituted benzyl group, a substituted or unsubstituted polyaromatic group, a substituted or unsubstituted vinyl group and a substituted or unsubstituted allyl group, $x \geq 2$, $y \geq 4$, in formula I, the Si/Al molar ratio is between 1.8 and 1.3 inclusive, and in formula II, M is chosen from the group composed of calcium, magnesium, zinc and strontium and mixtures of two or more thereof, and the Si/M molar ratio is between 1.8 and 1.3 inclusive.

The particles of the metal organosilicate polymer having formula I or formula II above, have particle sizes of between 10 and 100 nm.

The metal organosilicate polymers used in the invention are aluminosilicate compounds, or metal silicate compounds, comprising organic groups.

They are hygroscopic compounds. They may therefore contain a varying number of water molecules, which means that the number of hydroxyl groups in formulae I and II is variable. However, in order to adhere to the stoichiometry of these formulae, the number of hydroxyl groups is at least 2 in formula I and at least 4 in formula II.

In addition to their organosilicate characteristic, the polymers of formula I used in the invention are characterized by an Si/Al molar ratio of between 1.8 and 1.3 inclusive, and the polymers of formula II used in the invention are characterized by an Si/M molar ratio of between 1.8 and 1.3 inclusive.

They are formed by methods of controlled cohydrolysis comprising the treatment of one or more magnesium, zinc, calcium, strontium or aluminum salt and of a mixture of silane coupling agents of formula $R_xSi(OR^1)_{4-x}$ in which x is between 1 and 2 inclusive and $R^1$ is a hydrolysable group, with an alcoholic alkaline solution.

In certain embodiments, the R functions of the silane coupling agents include a basic group such as an amino group, and it is then not necessary to add an alcoholic alkaline solution, although a small amount of base may be necessary in order for the desired stoichiometric equivalence amount of base to be present. The metal (one or more of magnesium, zinc, calcium, strontium and aluminum)/silicon molar ratio is preferably maintained between 1 and 0.5 inclusive, and the alkali/metal molar ratio is preferably maintained between 1 and 0.5 inclusive.

Preferably, an alcoholic solution of sodium hydroxide, of potassium hydroxide or of lithium hydroxide, of diethylamine or of triethylamine, having a concentration of between 0.5 M and 5 M inclusive, preferably of approximately 3 M, is used.

Preferably, the alkoxy groups of the silane coupling agent ($OR^1$) are propoxy, ethoxy or methoxy groups.

As regards each R group present in the silane coupling agent, it is chosen, independently of the others, from the group formed by a substituted or unsubstituted, linear- or branched-chain alkyl group, a substituted or unsubstituted, linear or branched alkenyl group, a substituted or unsubstituted aryl group, a substituted or unsubstituted benzyl group, a substituted or unsubstituted vinyl group, a substituted or unsubstituted polyaromatic group and a substituted or unsubstituted allyl group.

Most preferably, each R is, independently of the others, an alkyl group or an alkenyl group, each being linear or branched, and substituted or unsubstituted, or a substituted or unsubstituted benzyl group or a substituted or unsubstituted vinyl group.

Most preferably, each R is, independently of the others, a $C_1$ to $C_{18}$, more preferably $C_2$ to $C_8$, alkyl or alkenyl group, or a benzyl group or a vinyl group, all these groups being substituted or unsubstituted.

Most preferably, each R is, independently of the others, a methyl group, an ethyl group, an n-propyl group, an n-butyl group, a vinyl group or a benzyl group, it being possible for each of these groups to be substituted or unsubstituted.

The appropriate substituent groups of the R group, and especially of the linear or branched alkyl or alkenyl groups, may be any substituent that is appropriate for affecting the desired hydrophilicity or hydrophobicity properties.

For example, each R group may be substituted with a basic group such as an amino group, including diamino and triamino substituents, a halogen atom, such as one or more fluorine, chlorine, bromine or iodine atom, but preferably a chlorine atom, an ether group, an ester group, a hydroxyl group, an acrylate group such as a methacrylate group, or any other leaving group or any other reactive group which will allow additional modifications, such as an epoxy group, or optionally substituted aryl groups.

Most preferably, the substituent of the R group is an alkyl group, an alkyl acrylate group, an aminoalkyl group, a chloroalkyl group, a sulfonic group, a carboxylic group or a phosphonic group, especially a methyl group, an ethyl group, an n-propyl group, an n-butyl group, a propyl methacrylate group, a 3-chloropropyl group or a 3-aminopropyl group.

Thus, the particles of metal organosilicate polymer may be functionalized so as to make it possible to obtain dispersions of a hydrophilic material in an organic solvent.

However, the particles of metal organosilicate polymer may also be designed so as to make it possible to obtain an aqueous dispersion of particles of a hydrophobic material.

For this, particles of at least one metal organosilicate polymer having formula I or formula II as defined above will be added to the particles of the hydrophobic material.

By virtue of these particles of metal organosilicate polymer, it is possible to obtain an aqueous dispersion of carbon nanotubes by mixing the carbon nanotubes with a metal organosilicate polymer as described above and which makes it possible to disperse particles of a hydrophobic material.

In a first preferred embodiment, the aqueous dispersion of carbon nanotubes comprises carbon nanotubes and particles of a metal organosilicate polymer having formula II in which M is magnesium and four of the R groups are $(CH_2)_3NH(CH_3)$ groups and four of the R groups are $C_6H_5$ groups.

In a second preferred embodiment, the invention provides an aqueous dispersion of carbon nanotubes comprising carbon nanotubes and particles of an organosilicate polymer compound of formula II in which M is Mg and four R groups are 3-aminopropyl groups and four R groups are phenyl groups.

In a third preferred embodiment, the invention provides an aqueous dispersion in which the metal organosilicate polymer is of formula II in which M is Mg and four of the R groups are 3-aminopropyl groups and four of the R groups are vinyl groups.

In these three preferred embodiments, in order to obtain stabilization of the aqueous dispersion of carbon nanotubes for at least one hour, the mass of nanotubes/mass of metal organosilicate polymer ratio is preferably greater than or equal to 0.5.

In order to obtain an aqueous dispersion of carbon nanotubes that is stable for at least three hours, the mass of carbon nanotubes/mass of metal organosilicate polymer particles ratio is 0.8.

In a second variant, the invention provides an aqueous dispersion of benzotriazole compounds, and more particularly of 2-(2'-hydroxy-5'-methylphenyl)benzotriazole.

In this variant, the particles of metal organosilicate polymer are preferably particles of a metal organosilicate polymer of formula II in which M is zinc and four of the R groups are $(CH_2)_3NH(CH_3)$ groups and four of the R groups are $C_6H_5$ groups.

This aqueous dispersion obtained may be used, in particular, for the production of a composition for protection against UV radiation, in particular when it is applied as a thin film.

In fact, UV radiation breaks the hydrogen bond which enables 2-(2'-hydroxy-5'-methylphenyl)benzotriazole to be aromatic, which means that this molecule absorbs UV photons.

Since, with time, a new hydrogen bond forms, this means that this molecule is a regeneratable "absorber" of UV photons.

However, although it acts as a UV screen, this molecule is very sensitive to oxidation.

Now, it has been noted that the addition of a metal organosilicate polymer according to the invention, not only makes it possible to disperse this molecule in water, but also protects it against oxidation.

In order to understand the invention more clearly, several embodiments will now be described by way of purely illustrative and nonlimiting examples.

EXAMPLE 1

Synthesis of Particles of Metal Organosilicate Polymer of Formula II in which M is Mg and Four R Groups are 3-Aminopropyl Groups and Four R Groups are Phenyl Groups 0.0191 mol of $MgCl_2.6H_2O$ is solubilized in 200 g of ethanol, and then an equimolar mixture of (3-aminopropyl)triethoxysilane and phenyltriethoxysilane (0.00955/0.00955) in 20 g of EtOH is rapidly added. The solution rapidly becomes opaque, and 0.0095 mol of NaOH in 20 g of EtOH is then added. The reaction medium is stirred at ambient temperature for 24 H. After filtration, the white precipitate is washed with 200 g of ethanol. The white powder obtained is dried at ambient temperature for two days. The yield calculated with respect to magnesium is 49%. The Mg/Si molar ratio measured by ICP-AES (Inductively Coupled Plasma Atomic Emission Spectrophotometry) is 0.7. The X-ray diffraction shows that the product is slightly crystalline. The metal organosilicate polymer obtained is completely water-dispersible, it can be washed by dialysis or by nanofiltration and/or ultrafiltration. The particle size measured by photon correlation spectroscopy is between 20 and 50 nm. The particle size measurements are carried out at polymer concentrations of between 5 and 30 g/l. No increase in particle size is noted in this concentration range.

EXAMPLE 2

Synthesis of Particles of a Metal Organosilicate Polymer of Formula II in which M is Mg and Four of the R Groups are 3-Aminopropyl Groups and Four of the R Groups are Vinyl Groups 0.0191 mol of $MgCl_2.6H_2O$ is solubilized in 200 g of ethanol, and then an equimolar mixture of (3-aminopropyl) triethoxysilane and vinyltrimethoxysilane (0.00955/0.00955) in 20 g of EtOH is rapidly added. The solution rapidly becomes opaque, and 0.0095 mol of NaOH in 20 g of EtOH is then added. The reaction medium is stirred at ambient temperature for 24 H. After filtration, the white precipitate is washed with 200 g of ethanol. The white powder obtained is dried at ambient temperature for two days. The yield calculated with respect to magnesium is 48%. The Mg/Si molar ratio measured by ICP-AES (Inductively Coupled Plasma Atomic Emission Spectrophotometry) is 0.65. The X-ray diffraction shows that the product is weakly crystalline. The metal organosilicate polymer obtained is completely water-dispersible, it can be washed by dialysis or by nanofiltration and/or ultrafiltration. The particle size measured by photon correlation spectroscopy is between 20 and 50 nm. The particle size measurements are carried out at metal organosilicate polymer concentrations of between 5 and 30 g/l. No increase in particle size is noted in this concentration range.

In the examples which follow, the effectiveness of the particles of metal organosilicate polymer according to the invention for obtaining aqueous dispersions of hydrophobic compounds, and in particular of carbon nanotubes and of 2-(2'-hydroxy-5'-methylphenyl)benzotriazole, was evaluated.

EXAMPLE 3

Synthesis of Particles of a Metal Organosilicate Polymer in which M is Mg and Four R Groups are 3-Aminopropyl Groups and Four R Groups are $CH_3(CH_2)_{17}$ Groups 9.75 g of $MgCl_2.6H_2O$ are solubilized in 160 ml of EtOH, and then an equimolar mixture (0.03 mol of $CH_3(CH_2)_{17}Si(OEt)_3$+0.03 mol of $NH_2(CH_2)_3Si(OEt)_3$) in 20 ml of EtOH is added with stirring at ambient temperature. The solution becomes slightly cloudy. 0.03 mol of KOH in 20 ml of EtOH is then added (KOH can be replaced with NaOH or LiOH or a trimethylamine organic base; however, the inorganic bases are preferred). A white precipitate is formed. The reaction medium is left stirring at ambient temperature for 12 H, and then filtered through a Büchner funnel. The white powder obtained is washed with 150 ml of EtOH and then dried at ambient temperature for two days. The yield calculated with respect to magnesium is 47%. The Mg/Si molar ratio measured by ICP-AES (Inductively Coupled Plasma Atomic Emission Spectrophotometry) is 0.7. The X-ray diffraction shows that the product is slightly crystalline. The metal organosilicate polymer obtained is completely water-dispersible, it can be washed by dialysis or by nanofiltration and/or ultrafiltration. The particle size measured by photon correlation spectroscopy is between 20 and 60 nm in water. The particle size measurements are carried out at metal organosilicate polymer concentrations of between 5 and 20 g/l. No increase in particle size is noted in this concentration range.

EXAMPLE 4

Aqueous Dispersion of Carbon Nanotubes

The carbon nanotubes used are provided by the company Arkema.

The evaluation protocol is the following: a known amount of nanotubes is mixed with osmotically treated water containing or not containing a metal organosilicate polymer, and the containers are stirred in a Turbulaa® orbital mixer (Schatz system) manufactured by W.A. Bachofen.AG at ambient temperature. The containers are subsequently left to stand for one hour, and the transmission of visible light by the supernatant medium is subsequently measured in quartz cells with a 1 mm optical pathway. 0% transmission means that nothing passes through and that the carbon nanotubes are therefore in suspension.

Several samples are prepared:

Sample 4A: 50 mg of Arkema carbon nanotubes with 2 ml of osmotically treated water.

Sample 4B: 50 mg of Arkema carbon nanotubes in 2 ml of a solution containing (30 g/l) of NaCl.

Sample 4C: 50 mg of Arkema carbon nanotubes in 2 ml of an aqueous colloidal sol of the metal organosilicate polymer obtained in example 3 (20 g/l).

Sample 4D: 50 mg of Arkema carbon nanotubes in 2 ml of an aqueous colloidal sol of the metal organosilicate polymer obtained in example 1 (30 g/l).

Sample 4E: 50 mg of Arkema carbon nanotubes in 2 ml of an aqueous colloidal sol of the metal organosilicate polymer obtained in example 2 (30 g/l).

All the reaction media studied are, before being brought into contact with the carbon nanotubes, completely transparent to visible light, the transmission thereof is therefore 100%.

The light transmission results obtained after bringing into contact with the carbon nanotubes are given in Table 1 below:

TABLE 1

| Samples | % light transmitted after one hour of settling | % light transmitted after 3 hours of settling |
|---|---|---|
| Sample 4A | 100 | 100 |
| Sample 4B | 97 | 98 |
| Sample 4C | 0 | 10 |
| Sample 4D | 0 | 0 |
| Sample 4E | 0 | 0 |

Even in a concentrated salt solution (example 4B), the suspension of carbon nanotubes is not stable, it ends up settling out. On the other hand, the presence of metal organosilicate polymer makes it possible to stabilize the suspension, forming a black ink which does not allow light to pass through. After one hour, the dispersions or suspensions containing a metal organosilicate polymer according to the invention are still stable.

After three hours, the dispersions or suspensions in which the metal organosilicate polymer bears unsaturated organic groups are still stabilized.

The carbon nanotubes/metal organosilicate polymer mass ratio is preferably 0.8.

It is also preferably greater than 0.5, because, below 0.5, to the eye, it appears to be more difficult to disperse the carbon nanotubes.

EXAMPLE 5

Synthesis of Particles of a Metal Organosilicate Polymer of Formula II in which M is Zn and Four of the R Groups are $(CH_2)_3NH(CH_2)_2$ Groups and Four R Groups are Benzyl $(C_6H_5)$ Groups 1.2 mol of $ZnCl_2.6H_2O$ are solubilized in 2900 g of ethanol, and 312 g of (3-aminopropyl)triethoxysilane are rapidly added. A white precipitate is rapidly formed, and the reaction medium is stirred at ambient temperature for 24H. After filtration, the white precipitate is washed with 2000 g of ethanol. The white powder obtained is dried at ambient temperature for two days. The yield calculated with respect to zinc is 48%. The Zn/Si molar ratio measured by ICP-AES (Inductively Coupled Plasma Atomic Emission Spectrophotometry) is 0.57. The X-ray diffraction shows that the product is slightly crystalline. The metal organosilicate polymer compound obtained is completely water-dispersible, it can be washed by dialysis or by nanofiltration and/or ultrafiltration. The particle size measured by photon correlation spectroscopy is between 20 and 30 nm. The particle size measurements are carried out at metal organosilicate polymer concentrations of between 5 and 35 g/l. No increase in particle size is noted in this concentration range.

EXAMPLE 6

Aqueous Dispersion of 2-(2'-hydroxy-5'-methylphenyl)benzotriazole 25 ml of an aqueous colloidal sol of the metal organosilicate polymer obtained in example 5 (10 g/l) are stirred at ambient temperature, and 200 mg of 2-(2'-hydroxy-5'-methylphenyl)benzotriazole are then added. This mixture is completely insoluble in water. The dispersion in the colloidal sol is very slow, it is accelerated when the beaker is irradiated from above with a UV lamp (4W centered at 365 nm).

The dispersion becomes clear and transparent in a few minutes. Without this irradiation, the dispersion is very slow or even impossible. The UV radiation breaks the hydrogen bond which confers planarity and therefore electron delocalization on the 2-(2'-hydroxy-5'-methylphenyl)benzotriazole, and by the same token its absorbance in the UV range, and the latter depolymerizes and is rapidly adsorbed by the metal organosilicate polymer.

The dispersion obtained is stable over time.

EXAMPLE 7

Use of the Aqueous Dispersion of 2-(2'-hydroxy-5'-methylphenyl)benzotriazole for the Production of a Composition for Protection Against UV Radiation 2-(2'-hydroxy-5'-methylphenyl)benzotriazole is a compound which absorbs UV photons and is therefore an excellent agent for protecting against UV radiation. By virtue of the use of a metal organosilicate polymer according to the invention, this compound can be used in an aqueous dispersion for the production of thin layers. However, it is sensitive to oxidation. The aim of this example is to show that the aqueous dispersion of this compound with a metal organosilicate polymer is stabilized with respect to oxidation and that this dispersion can thus be used for the production of a composition for protecting against UV radiation.

In order to measure the stabilization of 2-(2'-hydroxy-5'-methylphenyl)benzotriazole with respect to oxidation, thin layers of the following compositions are produced:

Composition 10A: 5 ml of the dispersion of 2-(2'-hydroxy-5'-methylphenyl)benzotriazole obtained above are introduced into a sol-gel formulation made from a 0.1 M alcoholic mixture of four molar equivalents of 3-glycidopropyltrimethoxysilane+1 molar equivalent of tetraethyl orthosilicate+5 ml of $H_2O$.

The 5 ml of $H_2O$ of the sol-gel formulation of the 0.1 M alcoholic mixture were thus substituted with 5 ml of the dispersion of 2-(2'-hydroxy-5'-methylphenyl)benzotriazole obtained in this example.

Composition 10B: 0.5 ml of the dispersion of 2-(2'-hydroxy-5'-methylphenyl)benzotriazole obtained in this example is introduced into the sol-gel formulation of the 0.1 M alcoholic mixture.

In this case, only 10% of the 5 ml of $H_2O$ of this sol-gel formulation is replaced with the aqueous dispersion of 2-(2'-hydroxy-5'-methylphenyl)benzotriazole obtained in this example.

Composition 10C: By way of comparison, a composition containing 100 mg of 2-(2'-hydroxy-5'-methylphenyl)benzotriazole not stabilized with a metal organosilicate polymer according to the invention, diluted in polyvinyl alcohol (4%), THF (25 ml) and water (10 ml), is prepared.

These compositions are deposited onto glass slides and dried.

Three thin layers, denoted respectively 10A, 10B and 10C, are then obtained.

All the layers obtained are completely transparent and homogeneous.

All the layers obtained screen out UV radiation in the 280 to 380 nm region. The percentage absorbed in the UV range is directly proportional to the amount of 2-(2'-hydroxy-5'-methylphenyl)benzotriazole present.

The transmittances of these thin transparent layers are measured:
- immediately after production thereof,
- after 48 hours in the dark under an extractor hood (10 $m^3$/h),
- after 24 hours under UV irradiation (4W centered at 365 nm) in air, and
- after 24 hours under UV radiation (4W centered at 365 nm) under argon.

The results obtained are reported in Table 2 below:

TABLE 2

| Samples | % transmittance immediately after production | % transmittance after 48 hours in the dark | % transmittance after 24 hours of UV exposure in air | % transmittance after 24 hours of UV exposure under argon |
|---|---|---|---|---|
| Thin layer 10A | 85% | 85% | 85% | 84% |
| Thin layer 10B | 10% | 10% | 10% | 11% |
| Thin layer 10C | 87% | 65% | 60% | 60% |

These results confirm that the metal organosilicate polymer of the invention stabilizes 2-(2'-hydroxy-5'-methylphenyl)benzotriazole against oxidation.

What is claimed is:
1. A method for forming a dispersion of a hydrophobic material in water or a dispersion of an organophobic material in an organic solvent, the method comprising contacting said material with at least one metal organosilicate polymer having the following formula I:

$$R_8Si_{8+x}M_6O_{16}(OH)_y$$ Formula I:

in which:
each R is, independently of the others, a group selected from the group consisting of a substituted or unsubstituted, linear or branched alkyl group, a substituted or unsubstituted, linear or branched alkenyl group, a substituted or unsubstituted aryl group, a substituted or unsubstituted benzyl group, a substituted or unsubstituted vinyl group, a substituted or unsubstituted polyaromatic group and a substituted or unsubstituted allyl group,
$-0.2 \leq x \leq 2.8$,
$y \geq 4$,
in formula I, M is chosen from the group consisting of calcium, magnesium, zinc and strontium and mixtures of two or more thereof, and the Si/M molar ratio is between 1.8 and 1.3 inclusive.

2. The method as claimed in claim 1, wherein, in formula I, each R is, independently of the others, chosen from a substituted or unsubstituted methyl group, a substituted or unsubstituted ethyl group, a substituted or unsubstituted n-propyl group, a substituted or unsubstituted benzyl group and a substituted or unsubstituted vinyl group.

3. The method as claimed in claim 1, wherein, in formula I, when R is substituted, it is substituted with at least one substituent selected from the group consisting of an amino group, a halogen atom, an ether group, an ester group, a hydroxyl group, an acrylate group, an epoxy group, an alkyl group, an alkyl acrylate group, an aminoalkyl group, a chloroalkyl group, a carboxylic group, a phosphonic group and a sulfonic group.

4. An aqueous dispersion of particles of a hydrophobic material, which comprises:
particles of at least one hydrophobic material, and
particles of at least one metal organosilicate polymer having one of the following formula I:

$$R_8Si_{8+x}M_6O_{16}(OH)_y$$ Formula I:

in which:
$-0.2 \leq x \leq 2.8$,
each R is, independently of the others, a group selected from the group consisting of a substituted or unsubstituted, linear or branched alkyl group, a substituted or unsubstituted, linear or branched alkenyl group, a substituted or unsubstituted aryl group, a substituted or unsubstituted benzyl group, a substituted or unsubstituted vinyl group, a substituted or unsubstituted polyaromatic group and a substituted or unsubstituted allyl group,
M is chosen from the group consisting of calcium, magnesium, zinc and strontium and mixtures of two or more thereof, and the Si/M molar ratio is between 1.8 and 1.3 inclusive.

5. The dispersion as claimed in claim 4, wherein, in formula I, each R is, independently of the others, chosen from a substituted or unsubstituted methyl group, a substituted or unsubstituted ethyl group, a substituted or unsubstituted n-propyl group, a substituted or unsubstituted benzyl group and a substituted or unsubstituted vinyl group.

6. The dispersion as claimed in claim 4, wherein, in formula I, when R is substituted, it is substituted with at least one substituent selected from the group consisting of an amino group, a halogen atom, an ether group, an ester group, a hydroxyl group, an acrylate group, an epoxy group, an alkyl group, an alkyl acrylate group, an aminoalkyl group, a chloroalkyl group, a carboxylic group, a sulfonic group and a phosphonic group.

7. The dispersion as claimed in claim 4, wherein the particles of hydrophobic material are carbon nanotubes.

8. The dispersion as claimed in claim 7, wherein the metal organosilicate polymer is of formula I in which M is magnesium and four R groups are —$(CH_2)_3NH(CH_3)$ groups and four R groups are $C_6H_5$ groups.

9. The dispersion as claimed in claim 7, wherein the metal organosilicate polymer is of formula I in which M is Mg and four R groups are 3-aminopropyl groups and four R groups are phenyl groups.

10. The dispersion as claimed in claim 7, wherein the metal organosilicate polymer is of formula I in which M is Mg and four of the R groups are 3-aminopropyl groups and four of the R groups are vinyl groups.

11. The dispersion as claimed in claim 7, wherein the mass of carbon nanotubes/mass of metal organosilicate polymer ratio is greater than or equal to 0.5.

12. The dispersion as claimed in claim 7, wherein the mass of carbon nanotubes/mass of metal organosilicate polymer ratio is equal to 0.8.

13. The aqueous dispersion as claimed in claim 4, wherein the hydrophobic material is 2-(2'-hydroxy-5'-methylphenyl)benzotriazole.

14. The aqueous dispersion as claimed in claim 13, wherein the metal organosilicate polymer is of formula I in which M is zinc and four R groups are —$(CH_2)_3NH(CH_3)$ groups and four R groups are $C_6H_5$ groups.

15. A composition for protecting against UV radiation comprising the aqueous dispersion as claimed in claim 13.

* * * * *